United States Patent
Kordes et al.

(10) Patent No.: US 7,494,663 B2
(45) Date of Patent: Feb. 24, 2009

(54) CYANOMETHYL TRITHIOCARBONATES AS NEMATICIDES

(75) Inventors: Markus Kordes, Frankenthal (DE); Wolfgang von Deyn, Neustadt (DE); Michael Hofmann, Ludwigshafen (DE); Thomas Schmidt, Neustadt (DE); Gerd Steiner, Kirchheim (DE); Michael F. Treacy, Corpus Christi, TX (US); Henry Van Tuyl Cotter, Raleigh, NC (US); Deborah L. Culbertson, Fuquay Varina, NC (US); Hong-Ming Shieh, Newton, PA (US)

(73) Assignee: BASF Aktiengesellschaft, Ludwigshafen (DE)

( * ) Notice: Subject to any disclaimer, the term of this patent is extended or adjusted under 35 U.S.C. 154(b) by 860 days.

(21) Appl. No.: 10/535,353

(22) PCT Filed: Nov. 21, 2003

(86) PCT No.: PCT/EP03/13108

§ 371 (c)(1),
(2), (4) Date: May 18, 2005

(87) PCT Pub. No.: WO2004/047534

PCT Pub. Date: Jun. 10, 2004

(65) Prior Publication Data

US 2006/0052442 A1    Mar. 9, 2006

Related U.S. Application Data

(60) Provisional application No. 60/428,255, filed on Nov. 22, 2002.

(51) Int. Cl.
*A01N 25/00* (2006.01)

(52) U.S. Cl. .................................................. 424/405
(58) Field of Classification Search .................. None
See application file for complete search history.

(56) References Cited

U.S. PATENT DOCUMENTS

| | | | |
|---|---|---|---|
| 2,676,129 A | | 4/1954 | Bashour |
| 3,180,790 A | * | 4/1965 | Goodhue .................... 514/512 |
| 4,197,311 A | * | 4/1980 | Wepplo et al. .............. 514/471 |
| 4,215,140 A | * | 7/1980 | Otto et al. .................... 514/512 |

FOREIGN PATENT DOCUMENTS

| | | |
|---|---|---|
| DE | 11045 | 1/1956 |
| DE | 122045 | 8/1966 |

* cited by examiner

*Primary Examiner*—Johann R Richter
*Assistant Examiner*—Tigabu Kassa
(74) *Attorney, Agent, or Firm*—Brinks Hofer Gilson & Lione

(57) ABSTRACT

The present invention relates to the use of compounds of formula (I), wherein R is $C_1$-$C_8$-alkyl, unsubstituted or substituted with 1, 2 or 3 radicals selected from the group consisting of halogen, amino, nitro, cyano, $C_1$-$C_4$-alkenyl, $C_1$-$C_4$-haloalkenyl, $C_1$-$C_4$-alkoxy, $C_1$-$C_4$-haloalkoxy, $C_1$-$C_4$-alkylthio, 5- to 10-membered heteroaryl containing as ring members 1, 2, 3 or 4 heteroatoms selected from oxygen, sulfur and nitrogen, and phenyl, wherein the heteroaryl and phenyl radicals may be substituted for the control of nematodes, a method for the control of nematodes, and a method for the protection of plants from infestation or attack by nematodes.

(I)

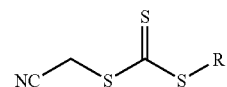

13 Claims, No Drawings

CYANOMETHYL TRITHIOCARBONATES AS NEMATICIDES

This application is a National Stage application of PCT/EP2003/013108 filed Nov. 21, 2003, which claims the benefit of U.S. Provisional Application No. 60/428,255, filed Nov. 22, 2002, the entire content of which is hereby incorporated by reference herein in its entirety.

The present invention relates to the use of cyanomethyl trithiocarbonates of the general formula I:

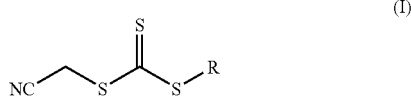

wherein R is $C_1$-$C_8$-alkyl, unsubstituted or substituted with 1, 2 or 3 radicals selected from the group consisting of halogen, amino, nitro, cyano, $C_1$-$C_4$-alkenyl, $C_1$-$C_4$-haloalkenyl, $C_1$-$C_4$-alkoxy, $C_1$-$C_4$-haloalkoxy, $C_1$-$C_4$-alkylthio, 5- to 10-membered hetaryl containing as ring members 1, 2, 3 or 4 heteroatoms selected from the group consisting of oxygen, sulfur and nitrogen, and phenyl, wherein the heteroaryl and phenyl radicals may be substituted with any combination of 1 to 5 halogen atoms, 1 or 2 cyano groups, 1 or 2 nitro groups, 1 to 3 $C_1$-$C_4$-alkyl groups, 1 to 4 $C_1$-$C_4$-haloalkyl groups, 1 to 3 $C_1$-$C_4$-alkoxy groups or 1 to 3 $C_1$-$C_4$-haloalkoxy groups for the control of nematodes.

DD 11 045 discloses insecticidally and nematicidally active acyclic and cyclic trithiocarbonates. With regard to their nematicidal activity preference is given to cyclic trithiocarbonates. Cyanomethyl trithiocarbonates are not disclosed therein.

Compounds of formula I wherein R is $C_1$-$C_8$-alkyl and their insecticidal and ovicidal activity have been described in U.S. Pat. No. 4,215,140. Insect and arachnid ovicidal activity of some of the compounds of formula I has also been taught in U.S. Pat. No. 4,197,311. Neither U.S. Pat. No. 4,215,140 nor U.S. Pat. No. 4,197,311 mention a nematicidal activity of compounds of formula I.

U.S. Pat. No. 2,676,129 teaches lower aliphatic di-substituted trithiocarbonates which carry saturated or unsaturated alkyl radicals at the sulfur atoms and having a total carbon content of from 3 to 9 carbon atoms. The compounds of U.S. Pat. No. 2,676,129 have a nematicidal activity. However, cyanomethyl trithiocarbonates are not disclosed therein.

In spite of the commercial nematicides available today, damage to crops caused by nematodes still occurs. Therefore, there is continuing need to develop new and more effective nematicidal agents.

It is therefore an object of the present invention to provide new nematicidal compositions and new methods for the control of nematodes and for protecting growing plants from attack or infestation by nematodes.

The inventors of the present invention have surprisingly found that these objects are achieved by cyanomethyl trithiocarbonate compounds of formula I and compositions comprising compounds of formula I.

The present invention thus provides a method for the control of nematodes by contacting a nematode or its food supply, habitat or breeding ground with a nematicidally effective amount of compounds of formula I or of compositions comprising them.

Moreover, the present invention also relates to a method of protecting growing plants from attack or infestation by nematodes by applying to the plants or the soil or water in which they are growing, a nematicidally effective amount of compounds of formula I or of compositions comprising them.

The compounds of formula I wherein R is $C_1$-$C_8$-alkyl are known from U.S. Pat. No. 4,215,140 and can be prepared as described therein. Moreover, all the compounds of formula I can be prepared following the procedures described in U.S. Pat. No. 4,215,140 and U.S. Pat. No. 4,197,311.

In the definitions of the symbols given in the above formula, collective terms were used which generally represent the following substituents:

Halogen: fluorine, chlorine, bromine and iodine.

Alkyl: straight-chain or branched saturated hydrocarbon group having 1 to 8 carbon atoms, e.g. $C_1$-$C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Alkenyl: straight-chain or branched unsaturated hydrocarbon group having 2 to 4 carbon atoms and a double bond in any position, such as ethenyl, 1-propenyl, 2-propenyl, 1-methyl-ethenyl, 1-butenyl, 2-butenyl, 3-butenyl, 1-methyl-1-propenyl, 2-methyl-1-propenyl, 1-methyl-2-propenyl, and 2-methyl-2-propenyl.

Halogenalkenyl: straight-chain or branched alkenyl groups having 2 to 4 carbon atoms (as mentioned above), where some or all of the hydrogen atoms in these groups may be replaced by halogen atoms as mentioned above.

Heteroaryl: a 5 to 10-membered heteroaromatic ring system containing 1 to 4 heteroatoms selected from oxygen, sulfur and nitrogen, e.g. 5-membered hetaryl, containing 1 to 4 nitrogen atoms or 1 to 3 nitrogen atoms and 1 sulfur or oxygen atom, e.g. furyl, thienyl, pyrrolyl, isoxazolyl, isothiazolyl, pyrazolyl, oxazolyl, thiazolyl, imidazolyl, oxadiazolyl, thiadiazolyl, oxadiazolyl, triazolyl, and tetrazolyl; or 5-membered hetaryl, containing 1 to 4 nitrogen atoms or 1 to 3 nitrogen atoms and 1 sulfur or oxygen atom, in which two adjacent ring carbon atoms or one nitrogen atom and an adjacent carbon atom can be bridged by buta-1,3-dien-1,4-diyl; or 6-membered hetaryl, containing 1 to 4 nitrogen atoms or 1 to 3 nitrogen atoms and 1 sulfur or oxygen atom, e.g. 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl;

With respect to the intended use of the compounds of formula I, preference is given to compounds of the formula I wherein R is $C_1$-$C_4$-alkyl, such as methyl, ethyl, propyl, isopropyl, n-butyl, 1-methylpropyl, 2-methylpropyl, and tert-butyl.

Furthermore, preference is given to compounds of the formula I wherein R is phenylethyl, benzyl, 4-chloro-benzyl, 4-fluoro-benzyl or 4-$C_1$-$C_3$-alkyl-benzyl.

Moreover, preference is given to the compound I wherein R is 2-furylmethyl.

Particular preference is given to the compound I wherein R is n-butyl.

The compounds of the formula I and compositions containing at least one compound of the formula I are useful for the control of nematodes, especially plant parasitic nematodes such as root knot nematodes, *Meloidogyne hapla*, *Meloidogyne incognita*, *Meloidogyne javanica*, and other

*Meloidogyne* species; cyst-forming nematodes, *Globodera rostochiensis* and other *Globodera* species; *Heterodera avenae, Heterodera glycines, Heterodera schachtii, Heterodera trifolii*, and other *Heterodera* species; Seed gall nematodes, *Anguina* species; Stem and foliar nematodes, *Aphelenchoides* species; Sting nematodes, *Belonolaimus longicaudatus* and other *Belonolaimus* species; Pine nematodes, *Bursaphelenchus xylophilus* and other *Bursaphelenchus* species; Ring nematodes, *Criconema* species, *Criconemella* species, *Criconemoides* species, *Mesocriconema* species; Stem and bulb nematodes, *Ditylenchus destructor, Ditylenchus dipsaci* and other *Dityienchus* species; Avwl nematodes, *Dolichodorus* species; Spiral nematodes, *Heliocotylenchus multicinctus* and other *Helicotylenchus* species; Sheath and sheathoid nematodes, *Hemicycliophora* species and *Hemicriconemoides* species; *Hirshmanniella* species; Lance nematodes, *Hoploaimus* species; false rootknot nematodes, *Nacobbus* species; Needle nematodes, *Longidorus elongatus* and other *Longidorus* species; Lesion nematodes, *Pratylenchus neglectus, Pratylenchus penetrans, Pratylenchus curvitatus, Pratylenchus goodayi* and other *Pratylenchus* species; Burrowing nematodes, *Radopholus similis* and other *Radopholus* species; Reniform nematodes, *Rotylenchus robustus* and other *Rotylenchus* species; *Scutellonema* species; Stubby root nematodes, *Tiichodorus prinmiivus* and other *Trichodorus* species, *Paratrichodorus* species; Stunt nematodes, *Tylenchorhynchus claytoni, Tylenchorhynchus dubius* and other *Tylenchorhynchus* species; Citrus nematodes, *Tylenchulus* species; Dagger nematodes, *Xiphinema* species; and other plant parasitic nematode species.

The compounds of formula I and compositions comprising them are especially useful for the control of *Meloidogyne* species, *Globodera* species, *Heterodera* species, *Pratylenchus* species, *Radopholus* species, *Rotylenchus* species, and *Tylenchulus* species. Most preferably, they are used for combating *Meloidogyne* species, *Globodera* species, and *Heterodera* species.

In practice generally about 0.1 ppm to about 10,000 ppm and preferably about 1 ppm to about 5,000 ppm of a composition or compound of formula I, dispersed in water or another liquid carrier, is effective when applied to plants or the soil or water in which the plants are growing or are to be grown to protect the plants from nematode infestation.

The compositions and compounds of the formula I and agricultural compositions containing at least one compound I are also effective for controlling nematode pests when applied to the pests or to their food supply, habitat or breeding ground or for protecting plants from attack or infestation by the nematodes when applied to the foliage, stem or roots of the plants and/or to the soil or water in which said plants are growing or are to be grown in sufficient amount to provide a rate of about 0.01 kg/ha to 100 kg/ha, preferably from about 0.1 to about 3.0 kg/ha, of active ingredient.

While the compositions and compounds of formula I are effective for controlling nematode pests of agronomic crops when employed alone, they may also be used in combination with other biological agents used in agriculture, including other nematicides, insecticides and/or acaricides. Mixing the compounds I or the compositions comprising them in the use form as pesticides with other pesticides frequently results in a broader pesticidal spectrum of action. For example, the formula I compounds of this invention may be used effectively in conjunction or combination with pyrethroids, phosphates, carbamates, cyclodienes, formamidines, phenol tin compounds, chlorinated hydrocarbons, benzoylphenyl ureas, pyrroles and the like. The following list of pesticides together with which the compounds according to the invention can be used, is intended to illustrate the possible combinations by way of example.

Organophosphates: Acephate, Azinphos-methyl, Chlorpyrifos, Chlorfenvinphos, Diazinon, Dichlorvos, Dicrotophos, Dimethoate, Disulfoton, Ethion, Fenitrothion, Fenthion, Isoxathion, Malathion, Methamidophos, Methidathion, Methyl-Parathion, Mevinphos, Monocrotophos, Oxydemeton-methyl, Paraoxon, Parathion, Phenthoate, Phosalone, Phosmet, Phosphamidon, Phorate, Phoxim, Pirimiphos-methyl, Profenofos, Prothiofos, Sulprophos, Triazophos, Trichlorfon;

Carbamates: Alanycarb, Benfuracarb, Carbaryl, Carbosulfan, Fenoxycarb, Furathiocarb, Indoxacarb, Methiocarb, Methomyl, Oxamyl, Pirimicarb, Propoxur, Thiodicarb, Triazamate;

Pyrethroids: Bifenthrin, Cyfluthrin, Cypermethrin, Deltamethrn, Esfenvalerate, Ethofenprox, Fenpropathrin, Fenvalerate, Cyhalothrin, LambdaCyhalothrin, Permethrin, Silafluofen, Tau-Fluvalinate, Tefluthrin, Tralomethrin, Zeta-Cypermethrin;

Arthropod growth regulators: a) chitin synthesis inhibitors: benzoylureas: Chlorfluazuron, Diflubenzuron, Flucycloxuron, Flufenoxuron, Hexaflumuron, Lufenuron, Novaluron, Teflubenzuron, Triflumuron; Buprofezin, Diofenolan, Hexythiazox, Etoxazole, Clofentazine; b) ecdysone antagonists: Halofenozide, Methoxyfenozide, Tebufenozide; C) juvenoids: Pyriproxyfen, Methoprene, Fenoxycarb; d) lipid biosynthesis inhibitors: Spirodiclofen;

Various: Abamectin, Acequinocyl, Amitraz, Azadirachtin, Bifenazate Cartap, Chlorfenapyr, Chlordimeform, Cyromazine, Diafenthiuron, Dinetofuran, Diofenolan, Emamectin, Endosulfan, Endotoxin of *Bacillus thuringiensis* (Bt), Fenazaquin, Fipronil, Formetanate, Formetanate Hydrochloride, Hydramethylnon, Imidacloprid, indoxacarb, Pyridaben, Pymetrozine, Spinosad, Sulfur, Tebufenpyrad, Thiamethoxam, and Thiocyclam.

The compounds of formula I and compositions comprising them can favorably be used for the simultaneous control of insect and nematode pests.

The compounds I can be converted into the customary formulations, e.g. solutions, emulsions, microemulsions, suspensions, flowable concentrates, dusts, powders, pastes and granules. The use form depends on the particular purpose; in any case, it should guarantee a fine and uniform distribution of the compound according to the invention.

The formulations are prepared in a known manner, e.g. by extending the active ingredient with solvents and/or carriers, if desired using emulsifiers and dispersants, it also being possible to use other organic solvents as auxiliary solvents if water is used as the diluent. Auxiliaries which are suitable are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. highly-disperse silica, silicates); emulsifiers such as non-ionic and anionic emulsifiers (e.g. polyoxyethylene fatty alcohol ethers, alkolsulfonates and arylsulfonates) and dispersants such as lignin-sulfite waste liquors and methylcellulose.

Suitable surfactants are alkali metal, alkaline earth metal and ammonium salts of lignosulfonic acid, naphthalenesulfonic acid, phenolsulfonic acid, dibutylnaphthalenesulfonic acid, alkylarylsulfonates, alkyl sulfates, alkylsulfonates, fatty alcohol sulfates and fatty acids and their alkali metal and alkaline earth metal salts, salts of sulfated fatty alcohol glycol ether, condensates of sulfonated naphthalene and naphthalene derivatives with formaldehyde, condensates of naphthalene or of napthalenesulfonic acid with phenol or formaldehyde, polyoxyethylene octylphenyl ether, ethoxylated isooctylphenol, octyiphenol, nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methylcellulose.

Substances which are suitable for the preparation of directly sprayable solutions, emulsions, pastes or oil dispersions are mineral oil fractions of medium to high boiling point such as kerosene or diesel-oil, furthermore coal tar oils and oils of vegetable or animal origin, aliphatic, cyclic and aromatic hydrocarbons, e.g. benzene, toluene, xylene, paraffin, tetrahydronaphthalene, alkylated naphthalenes or their derivatives, methanol, ethanol, propanol, butanol, chloroform, carbon tetrachloride, cyclohexanol, cyclohexanone, chlorobenzene, isophorone, strongly polar solvents, e.g. dimethylformamide, dimethyl sulfoxide, N-methylpyrrolidone and water.

Powders, materials for scattering and dusts can be prepared by mixing or concomitantly grinding the active substances with a solid carrier.

Granules, e.g. coated granules, compacted granules, impregnated granules and homogeneous granules, can be prepared by binding the active ingredients to solid carriers. Examples of solid carriers are mineral earths, such as silicas, silica gels, silicates, talc, kaolin, attaclay, limestone, lime, chalk, bole, loess, clay, dolomite, diatomaceous earth, calcium sulfate, magnesium sulfate, magnesium oxide, ground synthetic materials, fertilizers, e.g. ammonium sulfate, ammonium phosphate, ammonium nitrate, ureas, and products of vegetable origin, such as cereal meal, tree bark meal, wood meal and nutshell meal, cellulose powders and other solid carriers.

Such formulations or compositions of the present invention include a formula I compound of this invention (or combinations thereof admixed with one or more agronomically acceptable inert, solid or liquid carriers. Those compositions contain a pesticidally effective amount of said compound or compounds, which amount may vary depending upon the particular compound, target pest and method of use.

In general, the formulations comprise of from 0.01 to 95% by weight, preferably from 0.1 to 90% by weight, of the active ingredient. The active ingredients are employed in a purity of from 90% to 100%, preferably 95% to 100% (according to NMR spectrum).

The following are exemplary formulations:

I. 5 parts by weight of a compound according to the invention are mixed intimately with 95 parts by weight of finely divided kaolin. This gives a dust which comprises 5% by weight of the active ingredient.

II. 0.30 parts by weight of a compound according to the invention are mixed intimately with a mixture of 92 parts by weight of pulverulent silica gel and 8 parts by weight of paraffin oil which had been sprayed onto the surface of this silica gel. This gives a formulation of the active ingredient with good adhesion properties (comprises 23% by weight of active ingredient).

III. 10 parts by weight of a compound according to the invention are dissolved in a mixture composed of 90 parts by weight of xylene, 6 parts by weight of the adduct of 8 to 10 mol of ethylene oxide and 1 mol of oleic acid N-monoethanolamide, 2 parts by weight of calcium dodecylbenzenesulfonate and 2 parts by weight of the adduct of 40 mol of ethylene oxide and 1 mol of castor oil (comprises 9% by weight of active ingredient).

IV. 20 parts by weight of a compound according to the invention are dissolved in a mixture composed of 60 parts by weight of cyclohexanone, 30 parts by weight of isobutanol, 5 parts by weight of the adduct of 7 mol of ethylene oxide and 1 mol of isooctylphenol and 5 parts by weight of the adduct of 40 mol of ethylene oxide and 1 mol of castor oil (comprises 16% by weight of active ingredient).

V. 80 parts by weight of a compound according to the invention are mixed thoroughly with 3 parts by weight of sodium diisobutyinaphthalene-alpha-sulfonate, 10 parts by weight of the sodium salt of a lignosulfonic acid from a sulfite waste liquor and 7 parts by weight of pulverulent silica gel, and the mixture is ground in a hammer mill (comprises 80% by weight of active ingredient).

VI. 90 parts by weight of a compound according to the invention are mixed with 10 parts by weight of N-methyl-a-pyrrolidone, which gives a solution which is suitable for use in the form of microdrops (comprises 90% by weight of active ingredient).

VII. 20 parts by weight of a compound according to the invention are dissolved in a mixture composed of 40 parts by weight of cyclohexanone, 30 parts by weight of isobutanol, 20 parts by weight of the adduct of 7 mol of ethylene oxide and 1 mol of isooctylphenol and 10 parts by weight of the adduct of 40 mol of ethylene oxide and 1 mol of castor oil. Pouring the solution into 100,000 parts by weight of water and finely distributing it therein gives an aqueous dispersion which comprises 0.02% by weight of the active ingredient VIII. 20 parts by weight of a compound according to the invention are mixed thoroughly with 3 parts by weight of sodium diisobutylnaphthalene-a-sulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active ingredient.

The active ingredients can be used as such, in the form of their formulations or the use forms prepared therefrom, e.g. in the form of directly sprayable solutions, powders, suspensions or dispersions, emulsions, oil dispersions, pastes, dusts, materials for spreading, or granules, by means of spraying, atomizing, dusting, scattering or pouring. The use forms depend entirely on the intended purposes; in any case, this is intended to guarantee the finest possible distribution of the active ingredients according to the invention.

Aqueous use forms can be prepared from emulsion concentrates, pastes or wettable powders (sprayable powders, oil dispersions) by adding water. To prepare emulsions, pastes or oil dispersions, the substances as such or dissolved in an oil or solvent, can be homogenized in water by means of wetter, tackifier, dispersant or emulsifier. Alternatively, it is possible to prepare concentrates composed of active substance, wetter, tackifier, dispersant or emulsifier and, if appropriate, solvent or oil, and such concentrates are suitable for dilution with water.

The active ingredient concentrations in the ready-to-use products can be varied within substantial ranges. In general, they are from 0.0001 to 10%, preferably from 0.01 to 1%.

The active ingredients may also be used successfully in the ultra-low-volume process (ULV), it being possible to apply formulations comprising over 95% by weight of active ingredient, or even the active ingredient without additives.

Various types of oils, herbicides, fungicides, other pesticides, or bactericides may be added to the active ingredients, if appropriate also only immediately prior to use (tank mix). These agents can be admixed with the agents according to the invention in a weight ratio of 1:10 to 10:1.

Examples of Action Against Nematodes

The action of the compounds of formula I against nematodes for example is demonstrated for the compounds of table 1.

TABLE 1

| Compound No. | R |
|---|---|
| 1-1 | $(CH_2)_3CH_3$ |
| 1-2 | $CH_2-C_6H_5$ |
| 1-3 | $CH_2-(4-Cl-C_6H_4)$ |
| 1-4 | $CH_2-(4-CH_3-C_6H_4)$ |
| 1-5 | $(CH_2)_2-C_6H_5$ |

Nematicidal Evaluation

Test Procedures for Root-Knot Nematode Solution Assay (*Meloidogyne incognita*):

To microtiter plates containing about 1.0 mg of compound, 80:20 acetone was added to each well and the solution was mixed to obtain the desired compound concentration. The aqueous nematode suspension containing 20 to 50 *Meloidogyne incognita* J2 larvae per 50 ml was added to each plate. The plates were then sealed and they were placed in an incubator at 27° C. and about 50% relative humidity. After 72 hours, the population mortality was read, whereby immobility of nematodes was regarded as mortality.

In this test, compound 1.1 at 150 ppm showed 100% mortality compared to untreated controls.

Test Procedures for Soybean Cyst Nematode Solution Assay (*Heterodera glycine*):

To microtiter plates containing about 150 mg of compound, 80:20 acetone was added to each well and the solution was mixed to obtain the desired compound concentration. The nematode suspension of J2 *Heterodera glycines* larvae was added to the plate. The plates were then sealed and placed in an incubator at 27° C. and about 50% relative humidity. After 72 hours, the population mortality was read, whereby immobility of nematodes was regarded as mortality.

Soil nematicide assay targeting root-knot nematode, *Meloidogyne incognita*, and soybean cyst nematode, *Heterodera glycines*

The active ingredients were formulated by adding an appropriate amount (by weight) to an appropriate volume of acetone then adding 0.05% Tween® 20 (polyoxyethylene sorbitan monolaureate) in water for a final acetone concentration of 5% to achieve the desired concentration of active ingredient Dilutions were performed using the same carrier (5% acetone, 0.05% Tween® 20 in water).

Seedlings of soybean (cultvar Hutcheson) and seedlings of tomato (cultivar Bonny Best) were transplanted into individual planting cells containing a 1:1 mixture of sandy loam and coarse sand and kept in the greenhouse with bottom watering for one week. Then the preparation of the active ingredient was drenched on the soil surface to achieve known rates expressed as kg active ingredient per hectare soil surface (kg/ha). Later the same day aqueous suspensions of J2 nematode larvae, *Heterodera glycines* in the case of soybeans and *Meloidogyne incognita* in the case of tomatoes, were drenched on the soil surface. Plants were kept 1 day in a moist infection chamber at 26° C. and then maintained in the greenhouse with bottom watering until harvested for evaluation.

In the case of soybean cyst nematode on soybeans, plants were harvested 4 weeks after treatment and inoculation. Soil and roots were washed over a set of sieves to capture the nematode cysts which were then counted for each root system. Disease control efficacy against soybean cyst nematode was determined by calculating percent reduction in the number of cysts comparing the median number of cysts on the treated plants to the median number of cysts on inoculated soybean plants treated with the 5% acetone, 0.05% Tween® 20 carrier.

In the case of root knot nematode on tomatoes, plants were harvested 2 weeks after treatment and inoculation. The soil was washed off of the roots and the number of root knot galls on each root system was counted. Disease control efficacy against tomato root knot was determined by calculating percent reduction in root knot galling comparing the median number of galls on the treated plants to the median number of galls on inoculated tomato plants treated with the 5% acetone, 0.05% Tween® 20 carrier.

Treatments were replicated 3 times for each disease.

In this experiment, tomato plants that had been treated with 2.5 kg/ha of compounds I-2, I-3, I-4 and I-5 provided 100% reduction of root knot galling.

Soybeans plants that had been treated with 10 kg/ha of compounds 1-2 and 1-3 provided over 75% reduction of cysts.

The invention claimed is:

1. A method for the control of nematodes comprising contacting the nematodes or their food supply, habitat or breeding ground with a nematicidally effective amount of at least one compound of formula I:

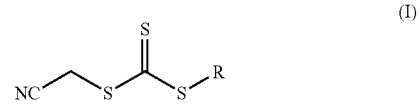

(I)

wherein R is $C_1$-$C_8$-alkyl, unsubstituted or substituted with 1, 2 or 3 radicals selected from the group consisting of halogen, amino, nitro, cyano, $C_1$-$C_4$-alkenyl, $C_1$-$C_4$-haloalkenyl, $C_1$-$C_4$-alkoxy, $C_1$-$C_4$-haloalkoxy, $C_1$-$C_4$-alkylthio, 5- to 10-membered heteroaryl containing as ring members 1, 2, 3 or 4 heteroatoms selected from oxygen, sulfur and nitrogen, and phenyl, wherein the heteroaryl and phenyl radicals may be substituted with any combination of 1 to 5 halogen atoms, 1 or 2 cyano groups, 1 or 2 nitro groups, 1 to 3 $C_1$-$C_4$-alkyl groups, 1 to 4 $C_1$-$C_4$-haloalkyl groups, 1 to 3 $C_1$-$C_4$-alkoxy groups or 1 to 3 $C_1$-$C_4$-haloalkoxy groups.

2. A method for the control of nematodes according to claim 1 wherein R is $C_1$-$C_4$-alkyl.

3. A method for the control of nematodes according to claim 1 wherein R is n-butyl.

4. A method for the control of nematodes according to claim 2 wherein R is n-butyl.

5. A method for the control of nematodes according to claim 1 wherein the nematodes are selected from the *Meloidogyne*, *Heterodera* and *Globodera* species.

6. A method for the control of nematodes according to claim 2 wherein the nematodes are selected from the *Meloidogyne*, *Heterodera* and *Globodera* species.

7. A method for the control of nematodes according to claim 3 wherein the nematodes are selected from the *Meloidogyne*, *Heterodera* and *Globodera* species.

8. A method for the protection of plants from infestation or attack by nematodes comprising applying to the plants or to the soil or the water in which they are growing a nematicidally effective amount of at least one compound of formula I:

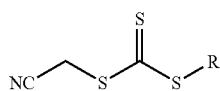

wherein R is $C_1$-$C_8$-alkyl, unsubstituted or substituted with 1, 2 or 3 radicals selected from the group consisting of halogen, amino, nitro, cyano, $C_1$-$C_4$-alkenyl, $C_1$-$C_4$-haloalkenyl, $C_1$-$C_4$-alkoxy, $C_1$-$C_4$-haloalkoxy, $C_1$-$C_4$-alkylthio, 5- to 10-membered heteroaryl containing as ring members 1, 2, 3 or 4 heteroatoms selected from oxygen, sulfur and nitrogen, and phenyl, wherein the heteroaryl and phenyl radicals may be substituted with any combination of 1 to 5 halogen atoms, 1 or 2 cyano groups, 1 or 2 nitro groups, 1 to 3 $C_1$-$C_4$-alkyl groups, 1 to 4 $C_1$-$C_4$-haloalkyl groups, 1 to 3 $C_1$-$C_4$-alkoxy groups or 1 to 3 $C_1$-$C_4$-haloalkoxy groups.

9. A method according to claim 8 wherein R is $C_1$-$C_4$-alkyl.

10. A method according to claim 8 wherein R is n-butyl.

11. A method according to claim 8 wherein the nematodes are selected from the *Meloidogyne, Heterodera* and *Globodera* species.

12. A method according to claim 9 wherein the nematodes are selected from the *Meloidogyne, Heterodera* and *Globodera* species.

13. A method according to claim 10 wherein the nematodes are selected from the *Meloidogyne, Heterodera* and *Globodera* species.

* * * * *